US009616073B2

(12) United States Patent
Ulmann et al.

(10) Patent No.: US 9,616,073 B2
(45) Date of Patent: *Apr. 11, 2017

(54) METHOD FOR ON-DEMAND CONTRACEPTION

(75) Inventors: Andre Ulmann, Paris (FR); Erin Gainer, Paris (FR); Henri Camille Mathe, Paris (FR); Lynnette Nieman, Bethesda, MD (US); Diana Blithe, Silver Spring, MD (US)

(73) Assignees: Laboratoire HRA-Pharma, Paris (FR); The United States of America, as represented by the Secretary, Department of Health and Human Services, Washington, DC (US)

( * ) Notice: Subject to any disclaimer, the term of this patent is extended or adjusted under 35 U.S.C. 154(b) by 55 days.

This patent is subject to a terminal disclaimer.

(21) Appl. No.: 13/263,717

(22) PCT Filed: Apr. 13, 2010

(86) PCT No.: PCT/EP2010/054812
§ 371 (c)(1),
(2), (4) Date: Jan. 30, 2012

(87) PCT Pub. No.: WO2010/119029
PCT Pub. Date: Oct. 21, 2010

(65) Prior Publication Data
US 2012/0122828 A1 May 17, 2012

Related U.S. Application Data

(60) Provisional application No. 61/169,149, filed on Apr. 14, 2009.

(51) Int. Cl.
A61K 31/57 (2006.01)
A61K 31/573 (2006.01)
A61K 9/00 (2006.01)
A61K 9/06 (2006.01)
A61K 31/56 (2006.01)
A61K 9/20 (2006.01)

(52) U.S. Cl.
CPC .......... *A61K 31/573* (2013.01); *A61K 9/0036* (2013.01); *A61K 9/06* (2013.01); *A61K 9/20* (2013.01); *A61K 31/56* (2013.01); *A61K 31/57* (2013.01)

(58) Field of Classification Search
None
See application file for complete search history.

(56) References Cited

FOREIGN PATENT DOCUMENTS

| WO | 00/09136 | 2/2000 |
|---|---|---|
| WO | WO0174840 | * 10/2001 |
| WO | 2008/079245 | 7/2008 |
| WO | 2008/122439 | 10/2008 |
| WO | 2010/066749 | 6/2010 |

OTHER PUBLICATIONS

Kuttenn et al. The Hormanal basis of discontinuous progestational contraception (author's transl.)] Nouv Presse Med. (1978) vol. 7, pp. 3109-3113.*
Reel et al. Antiovulator and Postcoital Antifertility Activity of the Antiprogestin CDB-2914 When Administered as Single, Multiple, or Continous Doses to Rats. Contraception (1998), vol. 58, pp. 129-136.*
Stratton et al. A single mid-follicular dose of CDB-2914, a new antiprogestin, inhibits folliculogenesis and endometrial differentiation in normally cycling women. Human Reproduction (2000), vol. 15, pp. 1092-1099.*
Aitman et al. Progress and pros[ects in rat genetics: a community view.(Nature Genetics (2008) vol. 40, pp. 516-522).*
Orihuela, Pedro A. "Ulipristal, a progesterone receptor antagonist as a contraceptive and for the treatment of uterine fibroids," Current Opinion in Investigational Drugs, PharmaPress, US. Oct. 1, 2007, vol. 8, No. 10; pp. 859-866.
International Search Report and Written Opinion for international application No. PCT/EP2010/054812 issued by the International Searching Authority mailed on Jul. 23, 2010.
"Complaint for Patent Infringement", U.S. District Court for the District of Delaware, *Laboratoire HRA Pharma v. Teva Pharmaceuticals USA, Inc.*, Case 1:15-cv-00045-UNA, Filed Jan. 16, 2015, 41 pgs.
"Report on the Filing or Determination of an Action Regarding a Patent or Trademark", Case 1:15-cv-00045-UNA, Filed Jan. 16, 2015, 1 pg.
FDA Study No. NCT00271583, "Efficacy Trial of CDB 2914 for Emergency Contraception" (2005).
FDA Study No. NCT00411684, "Safety and Efficacy of CDB-2914 for Emergency Contraception" (2006).
FDA Study No. NCT00551616, "Safety and Efficacy of CDB-2914 in Comparison to Levonorgestrol for Emergency Contraception" (2007).

* cited by examiner

*Primary Examiner* — Kendra D Carter
*Assistant Examiner* — Taina D Matos Negron
(74) *Attorney, Agent, or Firm* — Leason Ellis LLP

(57) ABSTRACT

The invention relates to a method for on-demand contraception, which method comprises administering a progestogen agent or progesterone receptor modulator, such as 17a-acetoxy-11b-[4-N,N-dimethylamino-phenyl]-19-norpregna-4,9-diene-3,20-dione (ulipristal acetate) in a woman, within 72 hours before an intercourse or within 120 hours after the intercourse.

4 Claims, No Drawings

METHOD FOR ON-DEMAND CONTRACEPTION

JOINT RESEARCH AGREEMENT

The present invention was made by or on behalf of parties to a joint research agreement that was in effect on or before the present invention was made. The present invention was made as a result of activities undertaken within the scope of the joint research agreement. Parties to the joint research agreement include Laboratoire HRA Pharma, and The United States of America, as represented by the Secretary, Department of Health and Human Services (the National Institutes of Health (the National Institute of Child Health and Human Development)).

The present invention relates to methods for on-demand contraception in a woman, especially women who do not have a regular sexual activity.

TECHNICAL BACKGROUND OF THE INVENTION

Hormonal contraception is considered the most reliable method of reversible contraception today. It requires the continuous taking of pills, generally daily, regardless of the frequency of intercourses. For women with infrequent sexual intercourse, however, preparations that are dependent on coitus and thus can be taken less often, with reduced exposure to the effective ingredients, would be more advantageous. Although recognized for a long time (Canzler et al, Zbl. Gynäkol, 1984, 106:1182-1191), the need for such on-demand contraception remains unmet (Aitken et al, Contraception, 2008, 78:S28-S35).

Women are actually creating such methods themselves out of existing products. In Ghana, a study conducted in 2003 reported that women were using norethindrone tablets, marketed for treatment of various gynecologic problems, as an "on demand" oral contraceptive. More recently, anecdotal reports and data collected by colleagues at Family Health International indicate that women in other parts of Africa and elsewhere are deliberately using emergency contraceptive pills in this manner.

Although oral methods do not provide protection against sexually transmitted infections, studies conducted several decades ago reported that various doses of levonorgestrel used as a regular postcoital contraceptive may provide protection with an efficacy comparable to the overall efficacy of condoms and other barrier methods in typical use (United Nations Development Programme/United Nations Population Fund/World Health Organization/World Bank Special Programme of Research, Development and Research Training in Human Reproduction, Task Force on Post-Ovulatory Methods of Fertility Regulation. Efficacy and side effects of immediate postcoital levonorgestrel used repeatedly for contraception. Contraception 2000; 61:303-8). It was further proposed to evaluate whether a single vaginal administration of levonorgestrel gel prior to intercourse would interfere with the ovulatory process. (Brache et al, Contraception, 2007; 76:111-116).

Other progestative agents have been used as post-coïtal emergency contraception. Emergency contraception (EC) refers to back-up methods for contraceptive emergencies which women can use within the first few days after unprotected intercourse to prevent an unwanted pregnancy. For instance the preclinical studies and the first clinical trials with ulipristal acetate, developed by HRA Pharma for emergency contraception, have proved that a single dose of 50 mg of ulipristal acetate is safe and efficacious when administered to women seeking emergency contraception within 72 hours after unprotected intercourse (Creinin et al, 2006, Obstetrics and Gynecology, 108(5):1089-1097).

SUMMARY OF THE INVENTION

The invention provides a method for contraception, which method comprises on-demand administering a progestogen agent or a progesterone receptor modulator in a woman, within 72 hours before an intercourse, which administration can be repeated at least once a week.

The invention also provides a method for contraception, comprising on-demand administering a progestogen agent or a progesterone receptor modulator thereof in a woman, within 120 hours after an intercourse, preferably at least twice a month.

In a preferred embodiment, the invention provides a method for contraception, which method comprises on-demand administering a progestogen agent or a progesterone receptor modulator thereof, such as 17a-acetoxy-11b-[4-N,N-dimethylamino-phenyl)-19-norpregna-4,9-diene-3,20-di-one (ulipristal acetate) or a metabolite thereof, in a woman, within 72 hours before an intercourse, which administration can be repeated at least once a week.

The invention also provides a method for contraception, comprising on-demand administering a progestogen agent or a progesterone receptor modulator thereof, such as 17a-acetoxy-11b-[4-N,N-dimethylamino-phenyl)-19-norpregna-4,9-diene-3,20-dione (ulipristal acetate) or a metabolite thereof, in a woman, within 120 hours after an intercourse, preferably at least twice a month.

DETAILED DESCRIPTION OF THE INVENTION

The inventors have studied whether ulipristal acetate could be used not only as an emergency contraceptive, but also as a regular hormonal contraceptive.

For that purpose, health cycling volunteers received 3 months of continuous daily administration of ulipristal acetate (2.5, 5 or 10 mg) or placebo.

Assessment of ovarian hormones, follicular development, endometrial histology, and menstrual bleeding patterns was carried out during the third month of treatment.

One patient (treated with 10 mg of ulipristal acetate/day) missed 2 days of drug in her third treatment cycle (days 1 and 2) and yet had no sign of luteal activity or ovulation. This made the inventors think that ulipristal acetate could be used as a contraceptive which could be taken on-demand, rather than everyday as any hormonal contraceptive pill.

On this basis, the invention provides a method for on-demand contraception, which method comprises administering a progestogen agent or progesterone receptor modulator, such as 17a-acetoxy-11b-[4-N,N-dimethylamino-phenyl)-19-norpregna-4,9-diene-3,20-dione (ulipristal acetate) or a metabolite thereof, in a woman, within 72 hours before an intercourse, and/or within 120 hours after an intercourse.

The invention further provides a method for contraception, which method comprises discontinously administering a progestogen agent or progesterone receptor modulator, such as ulipristal acetate or a metabolite thereof, in a woman. More particularly the progestogen agent or progesterone receptor modulator, such as ulipristal acetate or a metabolite thereof, may be administered less than once a day during the menstrual cycle. Preferably it is administered at least once a week during the menstrual cycle.

More generally, the inventors propose to use progestogen agents or progesterone receptor modulators for on-demand contraception.

Progestogen Agents:

The progestogen agents, also designated progestins, may be any progestationally active compound.

The progestogen agents may be selected from progesterone and its derivatives such as, for example, 17-hydroxy progesterone esters, 19-nor-17-hydroxy progesterone esters, 17α-ethinyltestosterone and derivatives thereof, 17α-ethinyl-19-nor-testosterone and derivatives thereof, norethindrone, norethindrone acetate, ethynodiol diacetate, dydrogesterone, medroxy-progesterone acetate, norethynodrel, allylestrenol, lynoestrenol, fuingestanol acetate, medrogestone, norgestrienone, dimethiderome, ethisterone, cyproterone acetate, levonorgestrel, DL-norgestrel, D-17α-acetoxy-13β-ethyl-17α-ethinyl-gon-4-en-3-one oxime, gestodene, desogestrel, norgestimate, nestorone and drospirenone.

In a preferred embodiment, it is to be understood that the progestogen agent is not combined with any other hormonal contraceptive agent, such as an estrogen. In that case, the contraceptive is often referred to as a "progestin-only" contraceptive.

Progesterone Receptor Modulators:

Progesterone receptor modulators for use in the present invention may be selected from e.g., ulipristal acetate, mifepristone or CDB-4124 or active metabolites thereof.

The preferred progesterone receptor modulator is ulipristal acetate.

Ulipristal acetate, formerly known as CDB-2914, is 17α-acetoxy-11β-[4-N,N-dimethylamino-phenyl]-19-norpregna-4,9-diene-3,20-dione, represented by formula I:

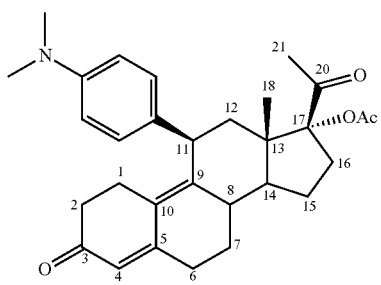

I

It is a well-known steroid, more specifically a 19-norprogesterone, which possesses antiprogestational and antiglucocorticoidal activity. This compound, and methods for its preparation, are described in U.S. Pat. Nos. 4,954,490, 5,073,548, and 5,929,262, and international patent applications WO2004/065405 and WO2004/078709. Properties of this compound are further described in Blithe et al, 2003, Steroids, 68:1013-1017 and Gainer and Ulmann, 2003, Steroids, 68:1005-1011.

Metabolites of CDB-2914, include those described in Attardi et al, Journal of Steroid Biochemistry & Molecular Biology, 2004, 88: 277-288, e.g. monodemethylated CDB-2914 (CDB-3877); didemethylated CDB-2914 (CDB-3963); 17alpha-hydroxy CDB-2914 (CDB-3236); aromatic A-ring derivative of CDB-2914 (CDB-4183).

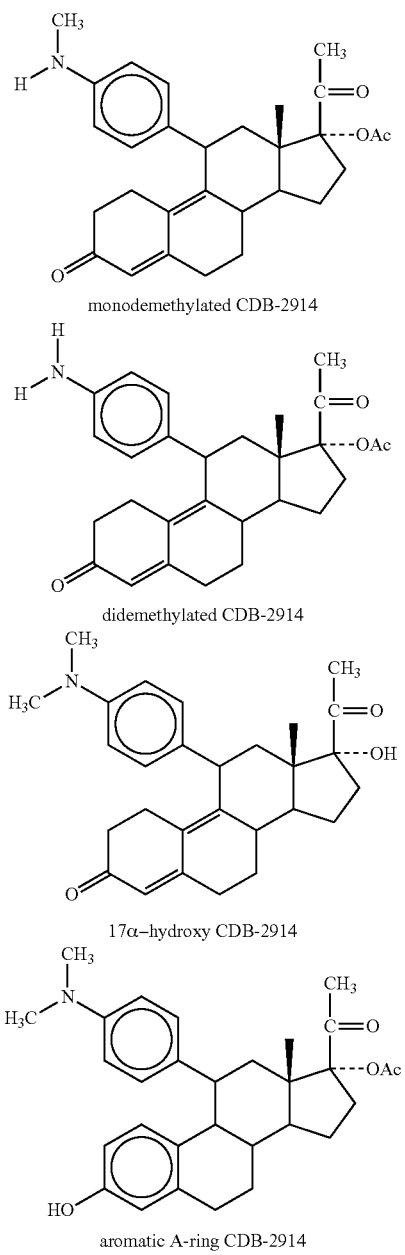

monodemethylated CDB-2914 didemethylated CDB-2914

17α-hydroxy CDB-2914 aromatic A-ring CDB-2914

On-Demand:

The subject or patient can be any human female. The invention provides an "on-demand contraception", which means that the woman may take a progestogen agent or progesterone receptor modulator, e.g. ulipristal acetate or a metabolite thereof at any time when needed, i.e. when an intercourse is expected, or has recently occurred. Preferably, the woman does not use any other hormonal contraceptive medication. In another preferred embodiment, the subject does not use any protection (condom, uterine device, spermicide, etc).

The woman may want to use the progestogen agent or progesterone receptor modulator, e.g. ulipristal acetate or a metabolite thereof, as a regular contraceptive when her sexual activity becomes more regular. Preferably the administration is then repeated at least once a week, preferably once a week or four times during a menstrual cycle, or twice during a menstrual cycle, or three times during a menstrual cycle. The term <<repeated>> means that one dosage unit of the progestogen agent or progesterone receptor modulator, e.g. ulipristal acetate or a metabolite thereof, is administered twice or more, during the menstrual cycle.

In any event, the woman always uses the progestogen agent or progesterone receptor modulator, e.g. ulipristal acetate or a metabolite thereof on-demand, and not on a daily basis, and preferably not more than ten days in a row, preferably not more than nine, eight, seven, six, five, four, three or two days in a row. Preferably the progestogen agent or progesterone receptor modulator, e.g. ulipristal acetate or a metabolite thereof is not administered more than four days, three or two days in a row.

Routes of Administration:

The progestogen agent or progesterone receptor modulator, e.g. ulipristal acetate or a metabolite thereof may be administered by any convenient route, including oral, buccal, sublingual, parenteral, transdermal, vaginal, rectal, etc.

For a brief review of present methods for drug delivery, see, Langer, Science 249:1527-1533 (1990), which is incorporated herein by reference. Methods for preparing administrable compounds are known or are apparent to those skilled in the art and are described in more detail in, for example, Remington's Pharmaceutical Science, 17th Ed., Mack Publishing Company, Easton, Pa. (1985), which is incorporated herein by reference, and which is hereinafter referred to as "Remington."

Unit dosages of immediate-release formulations are preferred.

For solid compositions, conventional nontoxic solid carriers may be used which include, for example, pharmaceutical grades of mannitol, lactose, starch, magnesium stearate, sodium saccharine, talcum, cellulose, glucose, sucrose. For oral administration, a pharmaceutically acceptable nontoxic composition is formed by incorporating any of the normally employed excipients, such as those carriers previously listed.

Oral solid dosage forms are preferentially compressed tablets or capsules. Compressed tablets may contain diluents to increase the bulk of the progestogen agent or progesterone receptor modulator so that production of a compressed tablet of practical size is possible. Binders, which are agents which impart cohesive qualities to powdered materials may be also necessary. Povidone, starch, gelatin, sugars such as lactose or dextrose, and natural and synthetic gums may be used. Disintegrants are generally necessary in the tablets to facilitate break-up of the tablet. Disintegrants include starches, clays, celluloses, algins, gums and crosslinked polymers. Lastly small amounts of materials known as lubricants and glidants are included in the tablets to prevent adhesion of the tablet material to surfaces in the manufacturing process and to improve the flow characteristics of the powder material during manufacture. Colloidal silicon dioxide is most commonly used as a glidant and compounds such as talc, magnesium stearate or stearic acids are most commonly used as lubricants. Procedures for the production and manufacture of compressed tablets are well known by those skilled in the art (See Remington).

Capsules are solid dosage forms using preferentially either a hard or soft gelatin shell as a container for the mixture of the progestogen agent or progesterone receptor modulator and inert ingredients. Procedures for production and manufacture of hard gelatin and soft elastic capsules are well known in the art (See Remington).

Buccal or sublingual forms or devices are also useful.

For parenteral administration, fluid unit dosage forms are prepared utilizing the compounds and a sterile vehicle, water being preferred. The progestogen agent or progesterone receptor modulator, depending on the vehicle and concentration used, can be either suspended or dissolved in the vehicle. In preparing solutions the compound can be dissolved in water for injection and filtered sterilized before filling into a suitable vial or ampoule and sealing. Advantageously, adjuvants such as a local anesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection is supplied to reconstitute the liquid prior to use. Parenteral suspensions can be prepared in substantially the same manner except that the compounds are suspended in the vehicle instead of being dissolved and sterilization cannot be accomplished by filtration. The compound can be sterilized by exposure to ethylene oxide before suspending in the sterile vehicle. Advantageously, a surfactant or wetting agent is included in the composition to facilitate uniform distribution of the progestogen agent or progesterone receptor modulator.

Additionally, a suppository or a pessary can be employed to deliver the progestogen agent or progesterone receptor modulator. The active compound can be incorporated into any of the known suppository bases by methods known in the art. Examples of such bases include cocoa butter, polyethylene glycols (carbowaxes), polyethylene sorbitan monostearate, and mixtures of these with other compatible materials to modify the melting point or dissolution rate. These suppositories can weigh from about 1 to 2.5 gm.

Transdermal delivery systems comprising a penetration enhancer and an occlusive backing are of use to deliver the progestogen agent or progesterone receptor modulator. Examples of penetration enhancers include dimethyl sulfoxide, dimethyl acetamide and dimethylformamide. Transcutaneous gels may be advantageous too. Examples of such gels are described e.g. in U.S. Pat. No. 5,904,931.

The progestogen agent or progesterone receptor modulator may be administered by vaginal route, for instance in the form of a gel or a vaginal device.

In another embodiment, the method of the invention comprises on-demand inserting a vaginal device, such as a vaginal ring that releases the progestogen agent or progesterone receptor modulator, in a woman, within 24 hours before or after an intercourse.

The vaginal ring usually comprises a synthetic polymer, which can be a silicone elastomer or a non-silicone resin. In a particular embodiment the ring comprises a polymer core, surrounded by an outer polymer layer comprising the progestogen agent or progesterone receptor modulator. In a particular embodiment, the ring is as described in international patent application WO2006/010097.

Preferably, the vaginal ring is removed within 12 hours after the intercourse. Most preferably, the vaginal ring is maintained in place for a minimum of 6 to 12 hours.

The oral route is preferred. Other routes of administration can be suitable in comparison with oral routes using blood levels to provide clinical success.

Dosages

The unit dosage of the progestogen agent or progesterone receptor modulator, e.g. ulipristal acetate or a metabolite thereof, may be between 10 and 40 mg, preferably 20 mg or 30 mg. Preferably the unit dosage of progestogen agent or progesterone receptor modulator, e.g. ulipristal acetate or a metabolite thereof is to be administered orally.

Regimen:

In a first embodiment of the invention, the progestogen agent or progesterone receptor modulator, e.g. ulipristal acetate or a metabolite thereof, can be administered within 72 hours before an intercourse, preferably within 48 h before the intercourse, more preferably within 24 h before the intercourse, still more preferably within 12 h before the intercourse.

In a second embodiment of the invention, the progestogen agent or progesterone receptor modulator, e.g. ulipristal acetate or a metabolite thereof can be administered within 120 hours after an intercourse, preferably within 72 h after the intercourse, more preferably within 48 h after the intercourse, still more preferably within 24 h after the intercourse, even more preferably within 12 h after the intercourse.

In a preferred embodiment, the administration is repeated at least twice a month, preferably three times a month or once a week.

For optimal efficiency, the two embodiments may be combined, i.e. a progestogen agent or progesterone receptor modulator, e.g. ulipristal acetate or a metabolite thereof, can be administered within 72 hours before an intercourse, and the same woman can also take a progestogen agent or progesterone receptor modulator, e.g. ulipristal acetate or a metabolite thereof, within 120 hours after the intercourse.

The following example is provided by way of illustration only and not by way of limitation.

EXAMPLE

Multiple Intakes of Ulipristal Acetate within a Menstrual Cycle

Several women received ulipristal acetate (30 mg) after a declared intercourse, twice during a menstrual cycle.

No pregnancy was observed.

| Patient | 1$^{st}$ intake | 2$^{nd}$ intake |
|---|---|---|
| Woman 1 | intercourse:<br>Dec. 11, 2007<br>06:00*<br>Ulipristal acetate intake:<br>Dec. 13, 2007<br>11:25 | intercourse:<br>Dec. 14, 2007<br>21:00<br>Dec. 14, 2007<br>14:37 |
| Woman 2 | intercourse:<br>Dec. 12, 2007<br>05:00<br>Ulipristal acetate intake:<br>Dec. 14, 2007<br>11:05 | intercourse:<br>Dec. 15, 2007<br>23:00<br>Ulipristal acetate intake:<br>Dec. 18, 2007<br>10:45 |
| Woman 3 | intercourse:<br>Dec. 15, 2007<br>06:00<br>Ulipristal acetate intake:<br>Dec. 17, 2007<br>11:40 | intercourse:<br>Dec. 15, 2007<br>22:00<br>Ulipristal acetate intake:<br>Dec. 18, 2007<br>11:15 |
| Woman 4 | intercourse:<br>Dec. 07, 2007<br>20:00<br>Ulipristal acetate intake:<br>Dec. 12, 2007<br>10:58 | intercourse:<br>Dec. 14, 2007<br>01:00<br>Ulipristal acetate intake:<br>Dec. 17, 2007<br>12:20 |
| Woman 5 | intercourse:<br>Nov. 2, 2007<br>08:00<br>Ulipristal acetate intake:<br>Nov. 5, 2007<br>15:00 | intercourse:<br>Nov. 5, 2007<br>06:00<br>Ulipristal acetate intake:<br>Nov. 8, 2007<br>15:30 |

*time are expressed in 24 hours format

The invention claimed is:

1. A method for on-demand contraception, comprising the step of administering a unit dosage of 30 mg of ulipristal acetate to a woman by oral route within 120 hours after an intercourse, wherein the administration is at least twice during the woman's menstrual cycle wherein the at least twice administration is not on the same day and no more than 3 days in a row during the woman's menstrual cycle.

2. The method of claim 1, wherein ulipristal acetate is administered at least once a week during the menstrual cycle.

3. The method of claim 1, wherein ulipristal acetate is not administered more than two days in a row.

4. The method of claim 1 wherein ulipristal acetate is administered as a tablet.

* * * * *